(12) United States Patent
Thorne, Jr.

(10) Patent No.: US 7,789,862 B2
(45) Date of Patent: Sep. 7, 2010

(54) MULTI-CHAMBER, SEQUENTIALLY DISPENSING SYRINGE

(75) Inventor: Gale H. Thorne, Jr., Bountiful, UT (US)

(73) Assignee: Thorne Consulting & Intellectual Property, LLC, Bountiful, UT (US)

( * ) Notice: Subject to any disclaimer, the term of this patent is extended or adjusted under 35 U.S.C. 154(b) by 0 days.

(21) Appl. No.: 11/899,254

(22) Filed: Sep. 5, 2007

(65) Prior Publication Data

US 2009/0062740 A1 Mar. 5, 2009

(51) Int. Cl.
*A61M 5/00* (2006.01)
*A61M 5/315* (2006.01)

(52) U.S. Cl. ........................ 604/191; 604/190; 604/231

(58) Field of Classification Search .................. 604/191, 604/187, 181; 606/92–94; 128/218
See application file for complete search history.

(56) References Cited

U.S. PATENT DOCUMENTS

| | | | |
|---|---|---|---|
| 3,736,932 A * | 6/1973 | Satchell | 604/190 |
| 4,929,230 A | 5/1990 | Pfleger | |
| 5,236,420 A | 8/1993 | Pfleger | |
| 5,298,024 A | 3/1994 | Richmond | |
| 5,713,857 A | 2/1998 | Grimard et al. | |
| 5,743,886 A * | 4/1998 | Lynn et al. | 604/191 |
| 5,899,881 A | 5/1999 | Grimard et al. | |
| 6,077,252 A | 6/2000 | Siegel | |
| 6,723,074 B1 | 4/2004 | Halseth | |
| 6,997,910 B2 | 2/2006 | Howlett | |
| 7,048,720 B1 | 5/2006 | Thorne, Jr. | |

* cited by examiner

*Primary Examiner*—Loan Thanh
*Assistant Examiner*—Imani Hayman
(74) *Attorney, Agent, or Firm*—Gale H. Thorne

(57) ABSTRACT

A discharge assembly is disclosed which partitions a conventional syringe into proximal and distal chambers to provide a multi-chamber, sequentially dispensing syringe apparatus. Incorporated in the discharge assembly is a syringe stopper body and an associated valve stem which in combination form a valve. A syringe plunger communicates through fluid in the proximal chamber to force displacement of the discharge assembly. The valve is actuated by collision between a rigid member which is a part of the valve stem and the distal internal surface of the syringe. The discharge assembly may be made from two parts: (1) the stopper body (made from conventional syringe stopper material); (2) the valve (actuating) stem made from rigid material similar to material from which the syringe barrel is made. Key features of such a multi-chamber syringe apparatus are (1) fluids in the chambers are kept disparate; (2) the discharge assembly may be used in conventional syringes; (3) gas in a closed chamber, proximal to the discharge assembly, is retained in the proximal chamber while only liquid is dispensed therefrom.

4 Claims, 8 Drawing Sheets

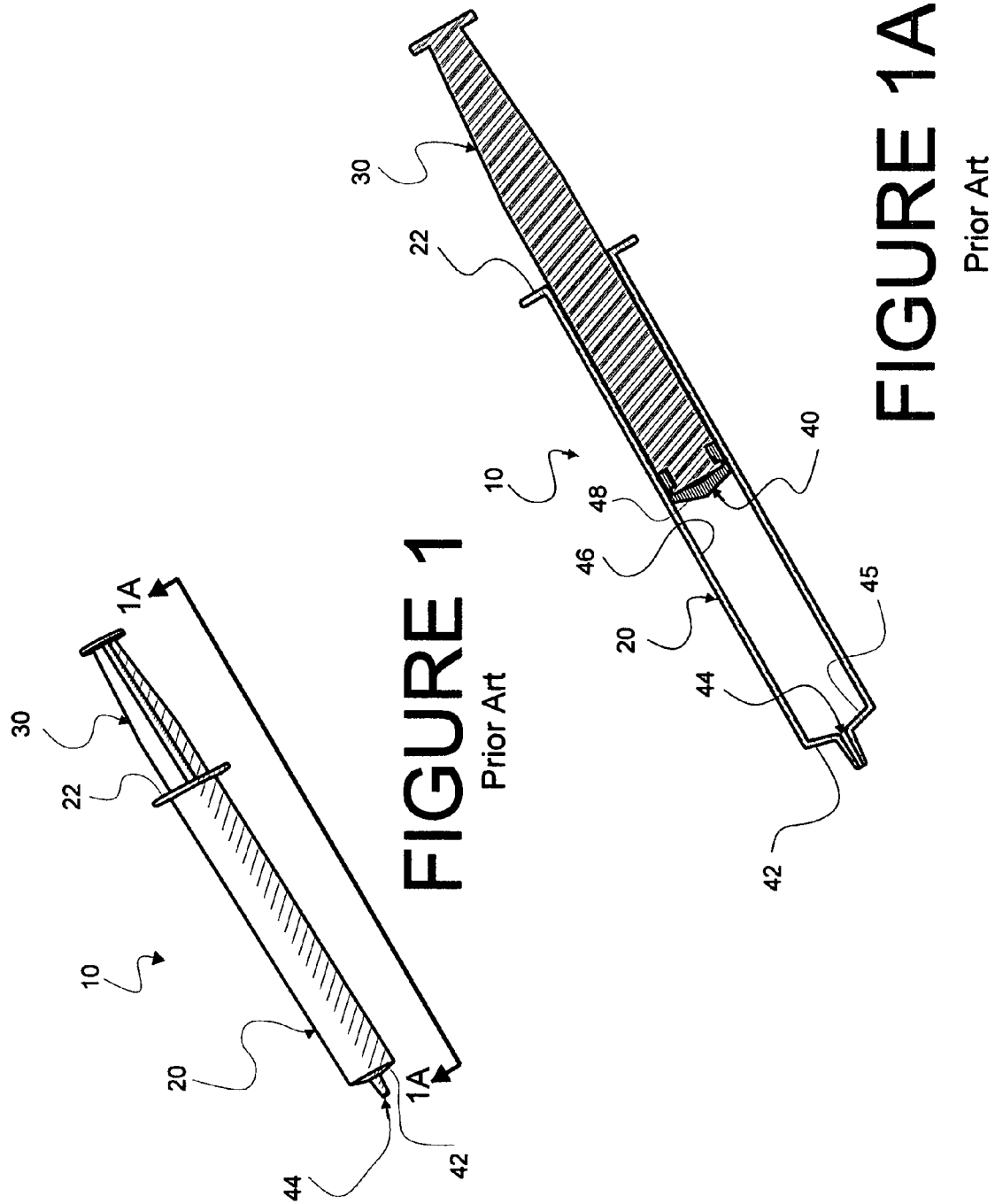

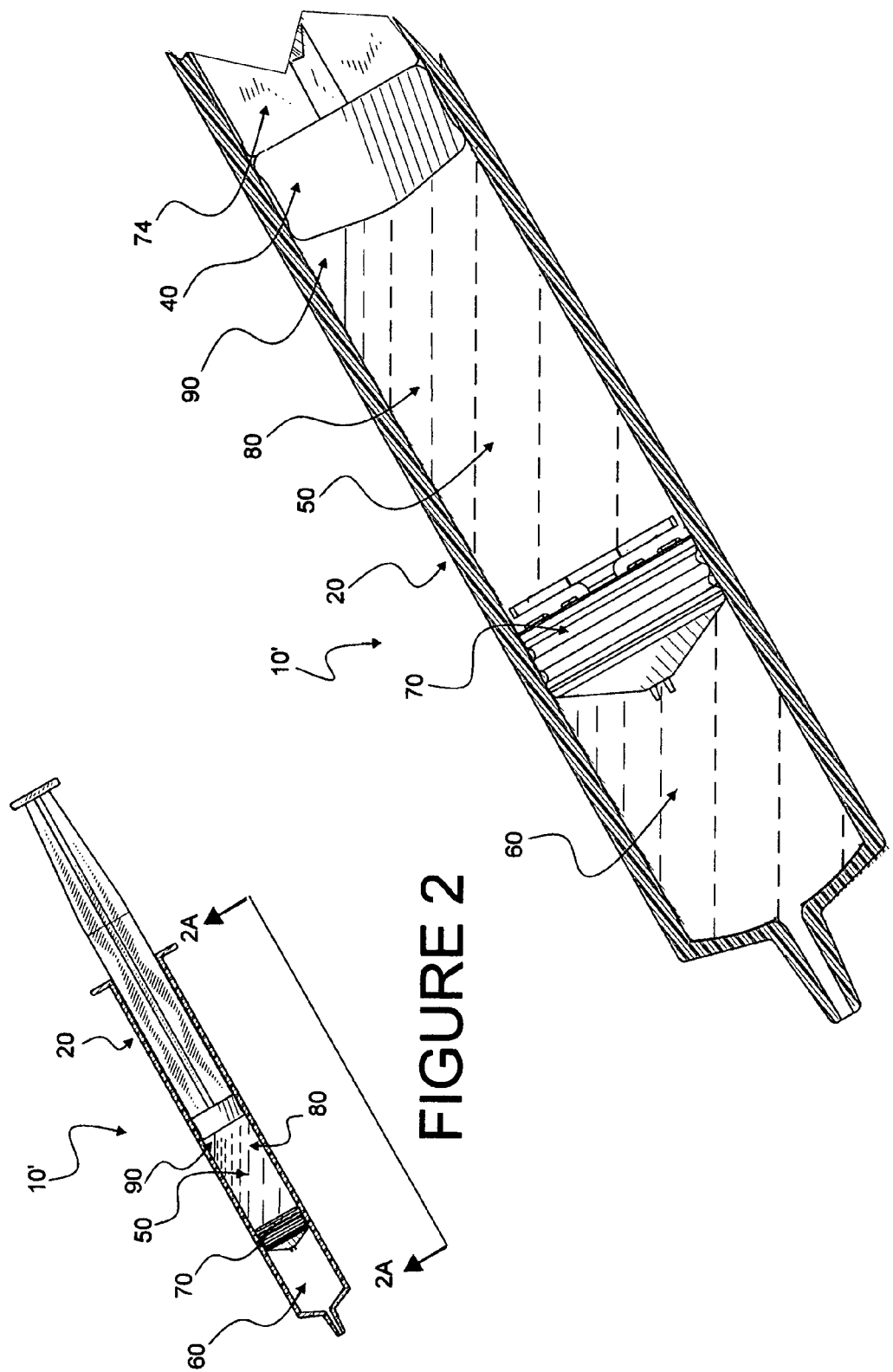

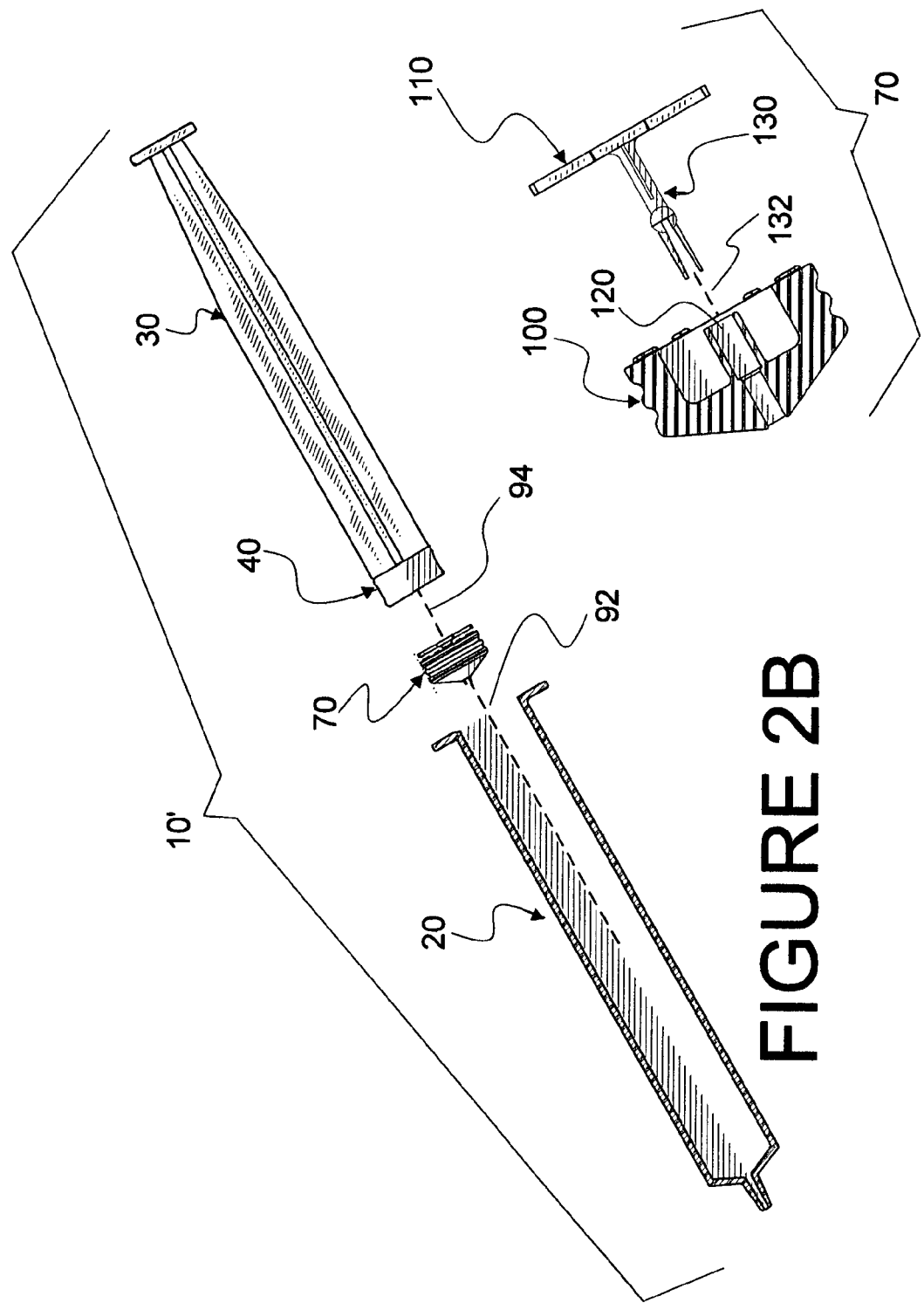

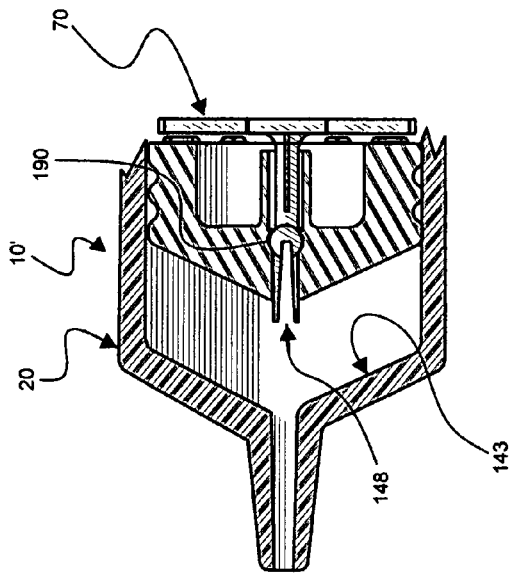
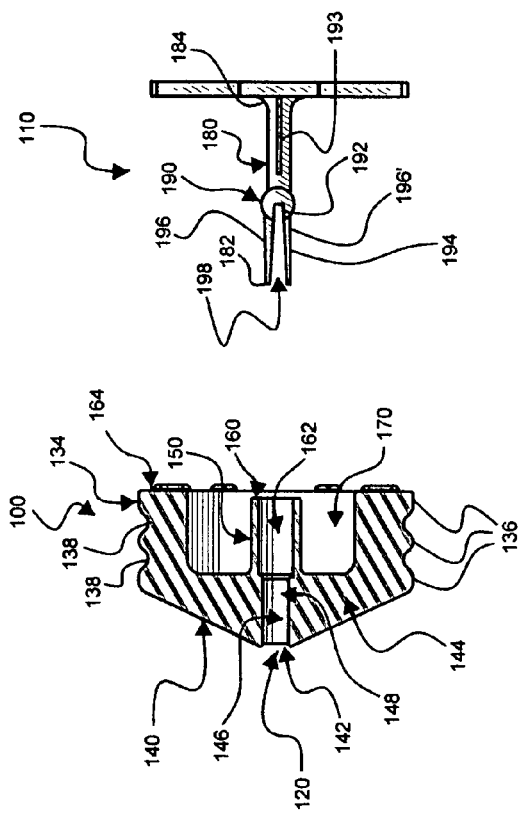
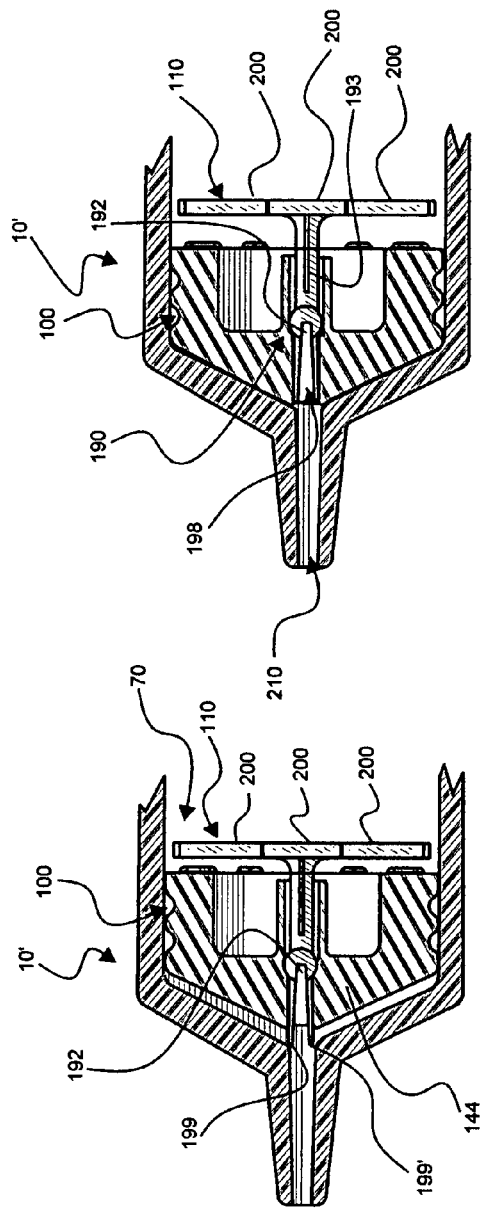

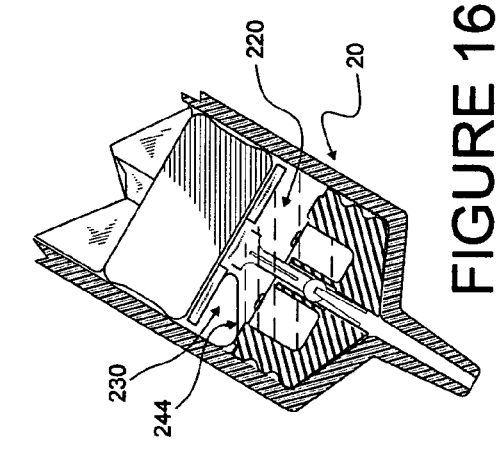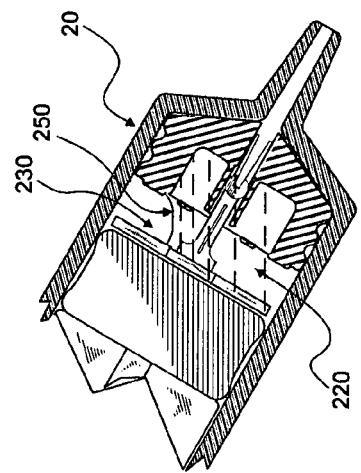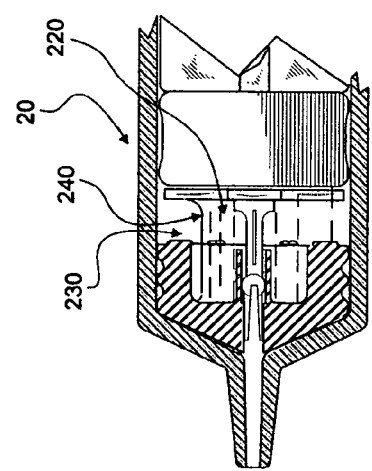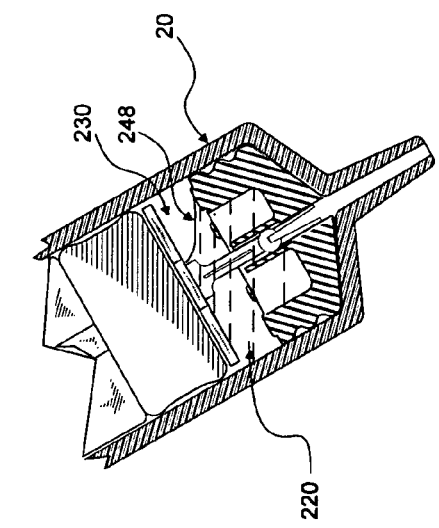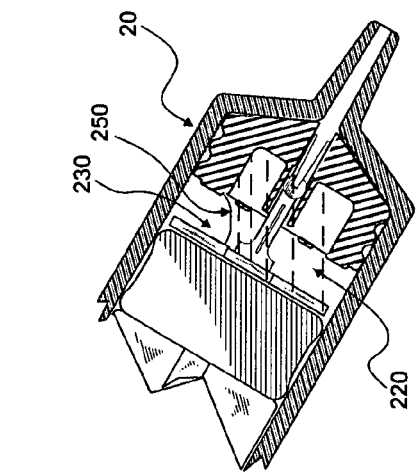

MULTI-CHAMBER, SEQUENTIALLY DISPENSING SYRINGE

FIELD OF INVENTION

This invention relates to multi-chamber syringes and, in particular, to multi-chamber syringes which employ conventional syringes and which dispense fluid sequentially from multiple chambers disposed within a single syringe barrel.

DESCRIPTION OF RELATED ART

Two recent U.S. patents disclose multi-chamber, sequential dose dispensing syringes from a conventional syringe barrel. A first is U.S. Pat. No. 6,997,910 B2, titled MULTI-CHAMBER, SEQUENTIAL DOSE DISPENSING SYRINGE was filed May 3, 2004 and issued Feb. 14, 2006 to Michael Wallace Howlett, et al. (Howlett 910). A second is U.S. Pat. No. 7,048,720 B1, titled MULTI-CHAMBER, SEQUENTIAL DOSE DISPENSING SYRINGE was filed Nov. 22, 2005 and issued May 23, 2006 to Gale H. Thorne, Jr., et al. (Thorne 720).

Thorne 720 recites that, "During the last forty years, parenteral drug delivery has become increasingly common and sophisticated. It is currently estimated that nearly 90% of hospital patients receive IV medications, often through a variety of apparatus, including expensive electronic IV pumps and multi-channel infusion systems. Home care patients may receive antibiotics through an elastomeric "ball" pump . . . ."

"Virtually all IV medications, administered through a catheter or IV tubing, must be flushed into the vascular system with saline or a similar physiologically compatible flushing fluid. Such flushing assures that a patient receives a full dose of medication, some of which otherwise might remain in the associated IV tubing or catheter. Flushing also assures that a subsequently infused incompatible medication does not come in contact with a previous one. It is well known in the infusion art that flush solutions are also used to keep an infusion line patent or open.

With rising healthcare costs, and an ever increasing shortage of nurses and pharmacists, there is a strong motivation to streamline basic procedures, such as IV catheter flushing to save clinician time. Noting that flushing usually necessitates use of a second flushing syringe (which is often currently factory pre-filled), the flushing syringe represents added cost, not only in clinician time, but in terms of required additional syringes. Use of multiple syringes also increases risk of medication error (incorrect selection of flushing liquid) and introduction of microorganisms (a function of number of IV line or catheter accesses).

As an example, it is currently estimated that there are over 500 million antibiotic and chemotherapy medications administered annually in the United States. Each of these administrations are taught to require a follow-on flush, currently necessitating use of a second syringe in most cases. Combining antibiotic or chemotherapy and flush medications in one multi-chamber, sequential dose syringe promises to save over 500 million syringes, yearly in the United States alone, plus that additional time required for two syringe delivery.

Multi-chamber syringes in various forms are well known. Commonly, multi-chamber syringes are offered for use as mixing syringes and for sequential delivery of disparate fluids, maintaining the fluids as disparate entities until delivered." Applicants of this instant invention concur with the above disclosed assessment.

As also taught in Thorne 720, "Generally, within each serial delivery syringe, chambers are separated by an intermediate sliding stopper which receives motive force communicated through an intermediate fluid from a primary stopper which is part of a plunger assembly against which an external force is applied. For disparate fluids to be dispensed sequentially or serially, each intermediate stopper must provide a fluid-tight seal until all fluid from a distal chamber is evacuated from the syringe. Once the distal chamber of the syringe is so purged, that intermediate stopper must be breached or bypassed to permit dispensing of the contents of a proximal or intermediate chamber."

Further, as initially disclosed in Howlett 910, "When prefilled doses are stored in the proximal chamber for ultimate use, it is not uncommon for gas (most commonly air) to collect in a non-[in]significant (corrected in Thorne 720) bubble size there inside. It is not good medical practice to dispense that gas into a patient line (e.g. an IV line). To preclude such an occurrence, the body comprises a gas separator. The gas separator is formed in a centrally disposed portion of the body and may be made as a hollow frustoconical shape, being open at the bottom. A series of very small, closely spaced holes are dispersed about the conical sides of the separator. The top of the frustoconical shape is closed except for a hole which is sufficiently large to permit purging gas from the separator. The open bottom of the separator (frustoconical shape) is disposed distally within the valved stopper into contact with the inner surface of the stopper about the slit. An outwardly projecting rim about the bottom of the separator provides an interlocking surface for a complimentary groove molded into the valved stopper about the slit."

It should be noted that solution for the problem of retaining gas within the proximal chamber as disclosed in Howlett 910 and Thorne 720 is an intermediary filter which passes liquid, but not gas. Such a filter must be purged of gas either in a manufacturing process or by other action prior to dispensing liquid from the proximal chamber. Thorne 720 discloses a slitted dome valve which inverts to an open state when the intermediate sliding stopper contacts the proximal face of an associated syringe barrel. It is Applicants' opinion that the filter disclosed in Howlett 910 and Thorne 720 can only be injection molded in relatively low cavitation molds, therefore limiting production efficiency and leading to increased cost. Similarly, a requirement to slit a molded part requires at least one additional step after molding, again leading to increased cost.

Another example of a multi-chamber syringe, as disclosed in Thorne 720, is provided in U.S. Pat. No. 4,929,230 titled SYRINGE CONSTRUCTION and issued May 29, 1990 to Frederick W. Pfleger (Pfleger). Pfleger discloses a distortable piston which is used as the intermediate stopper. A side of the piston of Pfleger collapses upon contact with a distal end of a syringe resulting in a fluid pathway to dispense contents from the proximal chamber.

Further, as disclosed in Thorne 720, while a syringe made, as an example, according to Pfleger provides a method for sequentially dispensing disparate fluids, a series of concerns would necessarily be associated with using such a syringe to dispense sequential doses of medications. A first concern arises when considering distal chamber dead space. For, when it is recognized that such a syringe may be desired to be used to dispense an accurately measured dose of a very expensive medication into an IV apparatus from a distal chamber of a multi-chamber syringe, dead space becomes an important issue. Also, immediately following dispensing of a first medication, a volume of a follow-on solution is dispensed through the IV line to fully flush the first solution.

Clearly, a deformable piston, having a hollow portion, such as the stopper of Pfleger does not have zero dead space. Also, it is well known that filling procedures for contents of the proximal chamber may permit a quantity of air (or other gas) to be trapped therein. It may be noted that even if such gas is not trapped during filling, free gas may be found in the proximal chamber simply as a result of out-gassing. Pfleger does not teach any means for purging the proximal chamber of gas or of retaining any gas in the proximal chamber while only dispensing liquid therefrom, making such a system unacceptable for delivering intravenous liquid medications to a patient. While other art may provide more effective ways to deal with dead space issues, only Howlett 910 and Thorne 720 teach a way of delivering only liquid from the proximal or intermediate chambers. That such may be a problem is recognized by U.S. Pat. No. 5,236,420 titled BYPASS, PRESSURIZED PISTON FOR CHAMBERS issued Aug. 17, 1993, also to Frederick W. Pfleger, discloses a valved plunger which may be used to evacuate gas from a proximal syringe chamber.

Another U.S. Pat. No. 5,298,024 titled MULTI-LIQUID MEDICAMENT DELIVERY SYSTEM WITH REFLEX VALVES issued Mar. 29, 1994 to Frank Richmond (Richmond) also discloses a sequential delivery syringe. Richmond utilizes a nipple integral with and disposed at the internal distal end of a syringe barrel to activate a valve assembly. No teachings or other matter associated with retarding dispensing gas from a chamber proximal to a valve assembly is provided in Richmond.

Thorne 720 cites additional art, such as U.S. Pat. Nos. 6,027,481 issued Feb. 22, 2000 to Laurent Barrelle, et al. (Barrelle) and 5,851,200 issued Dec. 22, 1998 to Tetsure Higashikawa, et al. (Hagashikawa) disclose multi-chamber syringes with sliding valves. However, in each case, Barrelle and Higashikawa teach special structure syringe barrel requirements (a channel in the case of Barrelle and a bulge in the case of Higashikawa) which provide a fluid pathway about a stopper.

Another U.S. Pat. No. 6,723,074 B1, titled SEQUENTIAL DELIVERY SYRINGE and issued Apr. 20, 2004 to Thor R. Halseth (Halseth), and also cited by Thorne 720, teaches a sequential delivery syringe which utilizes a modification for providing access to a rear chamber of a two chamber syringe. The modification comprises a piercing member at the distal syringe portal. The piercing member punctures a "mid-piston" and a collapsible bag disposed in a rear chamber to provide access to fluid in the bag. Proximal chamber access occurs when the mid-piston is displaced by action of a plunger and stopper piston to cause the mid-piston and bag to contact the piercing member.

DEFINITION OF TERMS

Following is a brief list of clarifying definitions for terms used in this application:

assembly n: a device which is made from at least two interconnected parts barrel n: a cylindrical elongated portion of a syringe which is conventionally open on one end to receive a plunger tip and plunger rod assembly used for displacing fluid within the barrel and partially closed at an opposite end except for an orifice or portal through which fluid is ejected or aspirated bi-stable adj: a descriptor for a device having two stable states bulbous adj: a mass which is sufficiently large in cross section to fill a hole chamber n: a volumetric portion of a divided barrel conduit sleeve n: an elongated tube affixed to a stopper whereby liquid is discharged from a chamber of a syringe conventional adj: sanctioned by general custom; i.e. commonplace, ordinary disparate n: when used in conjunction with a liquid volume, a volume of liquid which is distinctly separate from another liquid volume differential pressure ($\Delta P$) n: a pressure gradient resulting from unequal pressures exerted upon opposing sides of a structure; generally as used herein, $\Delta P = P_p - P_d$ distal adj: a term which depicts placement away from a reference point (e.g. away from a user of a syringe)

downstream adj: a direction which is consistent with flow out of a syringe or away from a user fluid n: a substance (e.g. a liquid or gas) which tends to take the shape of a container front adj/n: distally disposed or a distally disposed site (e.g. a front of a syringe comprises the barrel orifice)

gas n: a fluid which is neither solid nor liquid liquid n: a fluid which is neither solid nor gaseous, free flowing like water liquid zone n: a space within a syringe barrel which can only be physically occupied by liquid non-planar adj: not planar in a resting or stable state medial adj: occurring away from an outer edge; disposed near the center of (e.g. disposed away from an edge or periphery and in the vicinity of a center of gravity or axis of symmetry)

$P_d$ n: pressure in a distal chamber plunger rod n: a portion of a syringe piston apparatus, usually affixed to a plunger tip, to which force is applied to displace fluid within a syringe barrel plunger tip n: a portion of a syringe piston apparatus usually affixed to a plunger rod which is used to displace fluid within a syringe barrel prime v: to fill liquid into a cavity generally by removing air therefrom (e.g. priming a gas separator)

$P_p$ n: pressure in a proximal chamber proximal adj: opposite of distal (e.g. a term which depicts placement nearer to a reference point)

rear adj: opposite from front (i.e. generally associated with a part of a syringe barrel which is proximal to a syringe user)

reflux n: a type of undesired retrograde (upstream) flow of liquid (e.g. blood) into a catheter or the like from a vessel in which the catheter or the like resides state n: a mode or condition of matter, e.g. gaseous, liquid or solid stiction n: a special case of friction; stiction being the force required to initiate motion to a resting body, esp. when that force is greater than friction associated with a moving body stop n: an obstruction which is differentiated from friction or stiction which halts displacement of a stopper or plunger stopper n: a plunger associated with an assembly in a syringe which divides a portion of conventional syringe barrel into two disparate chambers, in the instant invention, the stopper providing a closed, but selectively openable pathway for liquid flow.

syringe n: a device used for injecting or withdrawing fluids upstream adj: a direction which is against the direction of flow from a syringe (opposite of downstream)

valve stem n: an elongated part which fits within a conduit sleeve of a stopper and provides a part of a normally closed valve

BRIEF SUMMARY AND OBJECTS OF THE INVENTION

In concert with the requirement of retaining gas in a more proximal chamber of a multi-chamber syringe, this invention provides unique constraints, structures and methods for sequentially dispensing liquids from each chamber of a syringe while assuring gas will not pass from the more proximal chamber.

The multi-chamber syringe apparatus according to the instant invention employs a conventional syringe barrel having an internal surface which is concentrically disposed about an elongated medial axis. In such syringes, the barrel surface has an open proximal end and a distal end having a closed interior about an orifice through which fluid is transferred.

Further, the multi-chamber syringe employs a plunger rod and plunger tip combination disposed to be displaced within said barrel by application of a directional force against said plunger rod for dislocating fluid thereby as is the case for conventional syringes.

The multi-chamber syringe configuration is formed by a discharge assembly disposed within the barrel between the plunger tip and the distal end. In this manner, a proximal chamber is created between the discharge assembly and plunger tip and a disparate distal chamber is provided between the discharge assembly and the closed interior surface.

A pre-fillable proximal chamber comprises space for fluid which comprises a gas globule (or globules) being limited, in total, to a predetermined volume, thereby only filling a portion of the chamber, and a quantity of liquid which fills space in the proximal chamber not taken by the gas.

The discharge assembly comprises a normally closed valve which is opened upon collision of the discharge assembly against the distal end of the syringe. Structure of the discharge assembly takes advantage of different state characteristics between gas and liquid residing within an elongated cylindrical chamber (e.g. the proximal chamber) to provide a liquid zone which is free of gas.

A conduit sleeve disposed in communication with the liquid zone through an access portal on a proximal end of the conduit sleeve and a normally closed valve, when opened, selectively, only permits liquid to be discharged from the proximal chamber. The valve is opened by collision of the discharge assembly with the distal end of the syringe.

In a preferred embodiment, the normally closed valve is an integral constituent of the discharge assembly. The discharge assembly preferably consists of two parts, a stopper and an elongated valve stem. The stopper generally has cylindrical exterior sides which are sized and shaped to provide a sliding seal at the interior wall interface of the syringe barrel.

Interiorly, the stopper is hollow, except for a distally disposed face section which is closed except for a medially disposed through hole and an elongated open tube affixed about the through hole and extending proximally to form the conduit sleeve which ends at an open portal, which is disposed within a liquid zone in the proximal chamber. (The liquid zone is medially disposed within the proximal chamber and is a natural consequence of gas being immiscible and much lighter than liquid and therefore being continuously thrust upward, against gravity, toward the highest point along the interior sides of the syringe barrel. Thereby, gas, of restricted volume, is physically evacuated from a predetermined medially disposed space or liquid zone.) In a device configured to meet requirements of the instant invention, the liquid zone occupies a proximally disposed space along the long medial axis of the barrel, a predetermined distance from the distal face of the stopper.

In a preferred embodiment, the stopper is molded of a pliant, elastic incompressible material, such as an elastomer. Thus, a portion of the stopper can be displaced to a different shape when a rigid member is forcibly imposed upon that portion, but memory within the stopper causes that portion to return to substantially the original shape when the rigid member is removed.

The valve stem is disposed through the conduit sleeve and through hole such that a distal end of the valve stem extends distally out of the through hole to provide an impact point between the discharge assembly and distal end of the syringe. A portion of the valve stem therefor resides within the through hole. That portion comprises a preferably bulbous section which is fully disposed within the through hole to displace a portion of sides of the through hole, providing a seal until removed. When the distal end of the valve stem collides with the distal end of the syringe, the valve stem is forcibly displaced proximally relative to the stopper, forcing the bulbous section outward from the through hole. Constricting material about space from which the bulbous section is displaced produces additional force to expel the bulbous section from the through hole. Once the bulbous section is fully expelled from the through hole, the conduit sleeve and through hole are opened for liquid flow from the portal and liquid zone. Thus, the valve stem and stopper, in combination, form a normally closed valve which is opened as a bistable valve upon impact of the discharge assembly with the distal end of the syringe.

Of course, it is critical that all contents of the distal chamber of the syringe be emptied before the valve opens. Such is accomplished through the use of memory of the stopper elastomer and shape of the bulbous section of the valve stem. Upon collision of the distal end of the valve stem and distal end of the barrel and following collision of the distal face of the stopper, the bulbous section is only partially removed from the through hole and the valve is not yet opened. After collision of the stopper and syringe distal end, pressure placed upon the stopper via the plunger rod further impacts stopper material about the through hole, providing lateral differential pressures which "squeeze" the bulbous section from the through hole, finally opening the valve.

To expedite expulsion of the bulbous section from the through hole, the bulbous section comprises a convex face toward the hole, which is accelerated from the through hole as stopper material memory shrinks sides of the through hole to substantially original size and shape.

To assure proper disposition of the open portal in the liquid zone, the valve stem preferably comprises a set of orthogonally disposed, proximal extensions which contact the interior wall of the syringe to align the valve stem along the medial axis of the barrel. The valve stem may be made from polypropylene or other material like that from which the barrel of the syringe is made.

In summary, the discharge assembly:
provides a selective partitioning between proximal and distal chambers of a multi-chamber syringe.
may be used in conventional (off the shelf) commercial syringes having constant diameter hollow barrels.
delivers fluid from a liquid zone within the proximal chamber, thereby only delivers liquid from the proximal chamber
permits the distal chamber of the syringe to be used in much the same manner as a conventional syringe prior to dispensing fluid from the proximal chamber.
provides a normally closed, bi-stable valve which is opened only after collision between the discharge assembly and inner surface of the distal end of the syringe and which remains in an open state once opened.
provides a visual object and a tactilely sensible force to open the valve after collision of the discharge assembly with the distal end of a syringe.
permits the valve to open only upon contact with a distal end of a syringe Accordingly, it is a primary object to provide a discharge assembly which partitions a conventional commercial syringe to make a multi-chamber syringe.

It is a fundamental object to provide a discharge assembly for a syringe which keeps two disparate fluids apart until one of the fluids has been dispensed from the syringe.

It is an important object to provide a discharge assembly which has a low dead space for liquid dispensed from a distal chamber.

It is a principal object to retain a predetermined volume of gas disposed in a chamber proximal to the discharge assembly in the proximal chamber while dispensing only liquid from the proximal chamber.

It is yet another object to provide a valve actuator within the discharge assembly which senses collision between the discharge assembly and an inner surface at the end of a syringe to force an associated valve open.

It is a critical object to provide a bi-stable valve as part of the discharge assembly.

It is another primary object to provide a discharge assembly which opens to dispense liquid from a proximal chamber only after liquid from a distal chamber has been dispensed.

It is a basic object to provide a discharge assembly which deters gas from being dispensed from the proximal chamber.

It is an object to provide an interface between a stopper and an associated rigid valve stem such that displacement of the stopper likewise displaces the rigid valve stem.

It is an object to provide a multi-chamber syringe having a front chamber which may be used in substantially the same manner as a conventional syringe prior to dispensing fluid from the proximal chamber.

These and other objects and features of the present invention will be apparent from the detailed description taken with reference to accompanying drawings.

BRIEF DESCRIPTION OF THE DRAWINGS

FIG. 1 is a perspective of a conventional syringe with an associated plunger rod.

FIG. 1A is a magnified cross section along lines 1A of the syringe and plunger rod seen in FIG. 1.

FIG. 2 is a perspective of a discharge chamber disposed in a conventional syringe barrel according to the instant invention.

FIG. 2A is a magnified cross section of a portion of the syringe barrel seen in FIG. 2 with proximal and distal chambers separated by the discharge assembly.

FIG. 2B is an exploded view of the parts including the discharge chamber, syringe barrel and a rear plunger assembly seen in FIG. 2.

FIG. 2C is an exploded view of the discharge assembly seen separately in FIG. 2B.

FIG. 3 is a cross section of a plunger portion of the discharge assembly seen in FIG. 2C.

FIG. 4 is a side elevation of a valve stem which is combined with the plunger portion seen in FIG. 3 to form the discharge assembly, seen in FIG. 2B.

FIG. 11 is a schematic of an untriggered discharge assembly formed by the combination of the plunger portion seen in FIG. 3 and the valve stem seen in FIG. 4 and disposed in a portion of a syringe barrel.

FIG. 12 is a schematic of the untriggered discharge assembly seen in FIG. 11 with a distal portion of a valve stem in contact with the distal face of the syringe barrel.

FIG. 13 is a schematic of the discharge assembly, seen in FIG. 11, disposed such that the valve stem is displaced proximally to provide an open valve.

FIG. 14 is a cross section of a portion of a barrel with a rear plunger assembly displaced to be disposed to provide a limited volume in the proximal chamber, the barrel being disposed orthogonal to gravity.

FIG. 15 is a cross section of a portion of a barrel seen in FIG. 14, but rotated 30 degrees counter clockwise.

FIG. 16 is a cross section of a portion of a barrel seen in FIG. 15, but rotated 30 degrees counter clockwise.

FIG. 17 is a cross section of a portion of a barrel seen in FIG. 16, but rotated 30 degrees counter clockwise.

FIG. 18 is a cross section of a portion of a barrel seen in FIG. 17, but rotated 30 degrees counter clockwise.

FIG. 19 is a cross section of a portion of a barrel seen in FIG. 18, but rotated 30 degrees counter clockwise.

DETAILED DESCRIPTION OF THE ILLUSTRATED EMBODIMENTS

Figure 10:
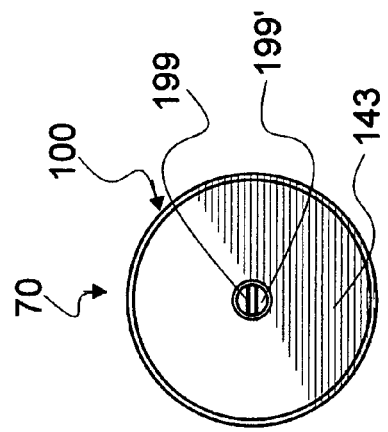
FIG. 10 is a lateral side elevation of the discharge assembly seen in FIG. 9 with the valving portion fully switched.

Reference is now made to embodiments illustrated in FIGS. 1-29 wherein like numerals are used to designate like parts throughout. In this description, primes of numbers are used to represent parts which are similar, but not identical to other parts having the same numbers.

Prior art syringes (as exemplified by syringe 10) in FIGS. 1 and 1A, are available from a large number of commercial companies worldwide. Such syringes typically comprise an elongated hollow syringe barrel 20 which is open at a proximal end 22 to receive a syringe plunger rod 30 and associated plunger tip 40 and closed at a distal end 42 about a fluid transmission orifice 44 through a distal face 45. Generally, barrel 20 is of substantially constant diameter (within tolerances allowed by manufacturing methods, such as by injection molding for barrels made from synthetic resinous materials or modeled from glass). Plunger tip 40 is compressible and sufficiently elastic when compressed to provide an efficient sealing and wiping action along the length of an internal cylindrical surface 46 of barrel 20. Generally a distal face 48 of plunger tip 40 is sized and shaped to conform with the distal internal face 45.

As seen in FIGS. 2 and 2A, a sequential delivery syringe 10', made according to the instant invention, is provided by disposing a discharge assembly 70 in a barrel 20. Thereby, barrel 20 is divided into a proximal chamber 50 and distal chamber 60. When proximal chamber 50 is filled, a volume of liquid 80 (along with a volume of gas 90) is captured, by a proximally disposed plunger tip 40 and plunger rod 74. Liquid volume 80 is predetermined by calculation of an amount of liquid desired to be dispensed from chamber 50. Gas volume 90 is limited to a maximum volume which is predetermined to not exceed that volume which establishes an adequate liquid zone. A liquid zone is defined to be a space within a syringe barrel wherein only liquid can physically occupy, application of which to the instant invention is disclosed in detail hereafter.

An exploded view of sequential delivery syringe 10' comprising a syringe barrel 20, a discharge assembly 70 and a plunger rod 30 and plunger tip 40 is seen in FIG. 2B. Assembly is straight forward. Discharge assembly 70 is displaced into syringe barrel 20 along dashed line 92 until a volume remaining in proximal chamber 50 (see FIG. 2A) is adequate for a desired liquid volume 80 and a gas volume 90. Plunger tip 40 is then inserted into syringe barrel 20 in along direction of line 94 to close chamber 50 (see FIG. 2A).

FIG. 2C is an exploded view of discharge assembly 70 wherein a plunger part 100 is disposed apart from a valve stem 110. Note that plunger part 100 comprises a medially disposed through hole 120 into which an elongated portion 130 of valve stem 110 may be inserted along direction of dashed line 132.

Plunger part 100 is seen in cross section in FIG. 3. Plunger part 100 is preferably molded from an elastomer material which is elastic, deformable, resilient and substantially incompressible. Such materials are commonly used in manufacture of plunger parts for syringes. Such plunger parts are generally molded to be oversized relative to syringe barrels in which they are placed to provide an orthogonal force against syringe walls to assure proper sealing and wiping as the plungers are displaced through an associated syringe barrel.

Plunger part 100 is likewise molded to be oversized relative to syringe barrel 20, with outside ringed cylindrical face 134 comprising ridges 136 and grooves 138 designed for wiping and sealing. A distal frustoconical face 140 is closed except for a distal opening 142 of through hole 120. Generally, face 140 is sized and shaped to conform with a distal internal surface 143 of syringe barrel 20 (See FIG. 11).

Proximal to face 140, part 100 comprises a thickened portion 144 which has an inner wall 146 which defines a distal segment 148 of hole 120. Proximal from portion 144, a hollow tubular section 150 extends proximally to a most proximal edge 160 to form a conduit sleeve. Tubular section 150 comprises a hollow 162 which communicates and shares a common longitudinal axis with distal segment 148. Hollow 162 comprises a cross section which is larger than the joining cross section of distal segment 148.

Plunger part 100 further comprises a hollow cylindrical side member 164 which provides inward support for face 134. Side member 164 is proximally open and distally closed by portion 144. Medially, tubular section 150 extends distally from portion 144 to form a washer shaped cavity 170 about tubular section 150.

As seen in FIG. 4, valve stem 110 comprises an elongated stem portion 180 having a distal end 182 and proximal end 184. Disposed between ends 182 and 184, portion 180 comprises a bulbous member 190. Bulbous member 190 is sized and shaped (e.g., in this case, a spherical shape) to compressibly fit into segment 148, thereby causing hole 120 to be closed and sealed when bulbous member 190 is disposed therein.

Further bulbous member 190 comprises at least one distally disposed groove 192 which is sufficient in cross section that liquid can flow therethrough. Distal from bulbous member 190, stem portion 180 extends to provide a trigger which is sized and shaped to collide with the associated distal internal surface 143 of syringe barrel 20. Note that juxtaposed sides 196 and 196' are separated to define a duct 198 which is contiguous with groove 192 thereby permitting distal fluid flow. Thus, when bulbous member 190 is fully enclosed within hole 148, no fluid can flow and a seal thereby created an associated valve is closed.

However, when that portion of bulbous member 190 is displaced to provide fluid access to groove 192 fluid can flow through from hollow 162 through groove 192 and duct 198 to be dispensed from syringe barrel 20. It should be further noted that hollow 162 must be large enough in cross section to permit flow about bulbous member 190 into groove 192. An elongated rib 193 (see FIGS. 4 and 13) is sized and shaped to aid such flow.

Valve stem 110 is preferably made from a rigid synthetic resinous material. To reduce material concerns relative to biological materials, it is preferred to make valve stem 110 from the same material used in syringe barrel 20.

Figure 5:
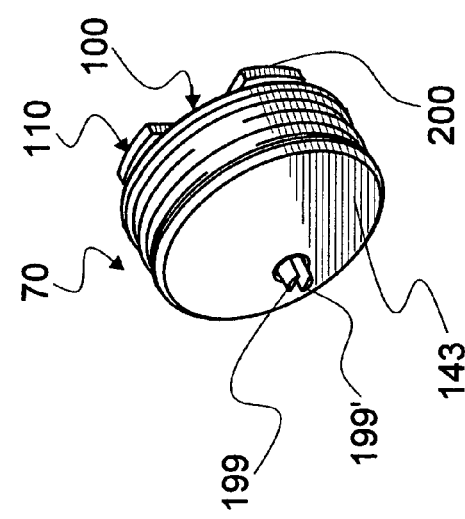
FIG. 5 is a perspective showing a distal face of an untriggered discharge assembly.
Figure 21:
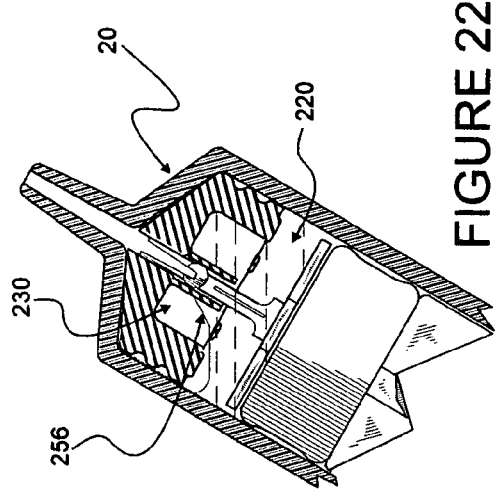
FIG. 21 is a cross section of a portion of a barrel seen in FIG. 20, but rotated 30 degrees counter clockwise.
Figure 20:
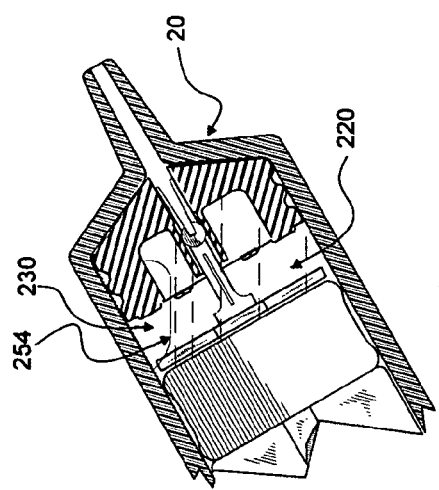
FIG. 20 is a cross section of a portion of a barrel seen in FIG. 19, but rotated 30 degrees counter clockwise.
Figure 22:
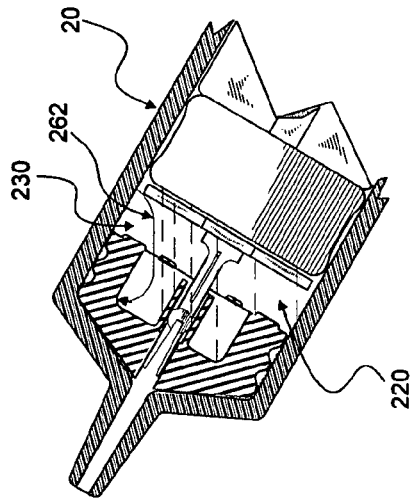
FIG. 22 is a cross section of a portion of a barrel seen in FIG. 21, but rotated 30 degrees counter clockwise.
Figure 25:
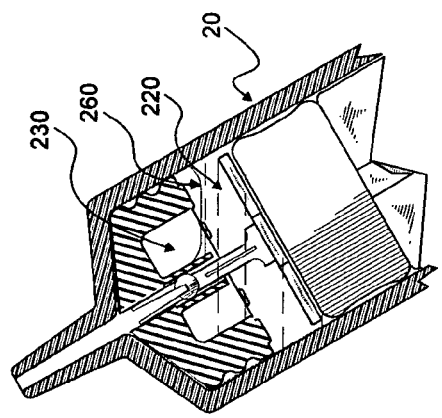
FIG. 25 is a cross section of a portion of a barrel seen in FIG. 24, but rotated 30 degrees counter clockwise.
Figure 24:
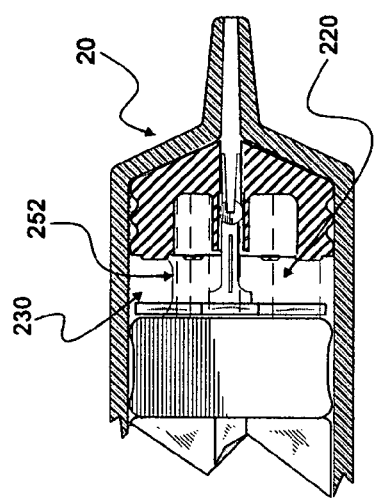
FIG. 24 is a cross section of a portion of a barrel seen in FIG. 23, but rotated 30 degrees counter clockwise.
Figure 23:
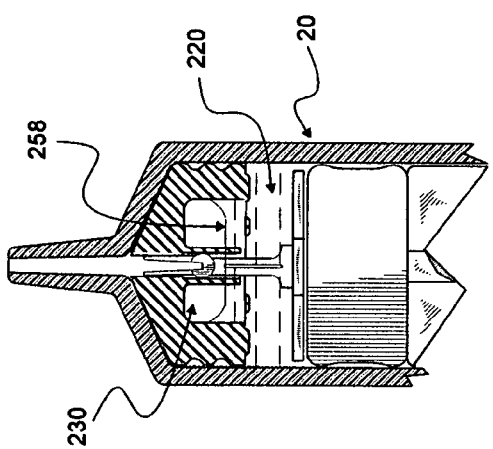
FIG. 23 is a cross section of a portion of a barrel seen in FIG. 22, but rotated 30 degrees counter clockwise.

Reference is now made to FIGS. 5-10 wherein discharge assembly 70 is seen in various states of operation. In FIG. 5, distal ends 199 and 199' of sides 196 and 196', respectively, are seen protruding from frustoconical face 140. In this state, ends 199 and 199' are disposed to collide with a distal internal surface 143 of an associated syringe barrel 20. Motive forces generally resulting from depressing a syringe plunger rod (such as rod 30 seen in FIGS. 1 and 1A) delivered through fluid contained in chamber 50 (see FIG. 2A) displace discharge assembly 70.

Figure 9:
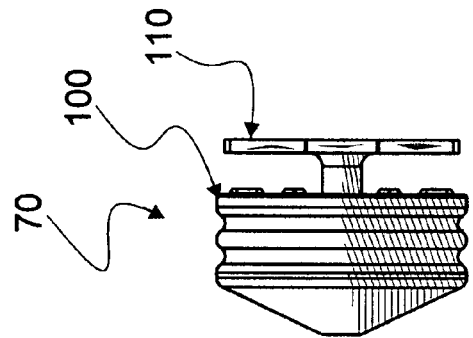
FIG. 9 is a lateral side elevation of the discharge assembly seen in FIG. 8 wherein a valving portion is partially switched.
Figure 8:
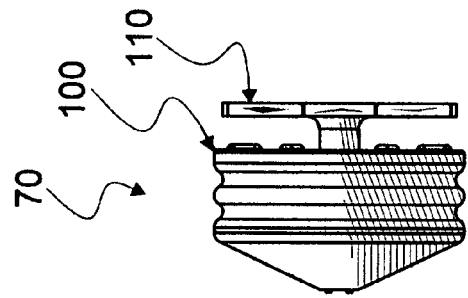
FIG. 8 is a lateral side elevation of the discharge assembly seen in FIG. 5.

Distal displacement ultimately results in collision of at least one end 199 or 199' with surface 143. When such occurs, valve stem 110 is sequentially displaced as seen in FIGS. 8-10. In FIG. 8, valve stem is in a state where an associated valve is closed. (Note ends 199 and 199' extending distally from surface 143.)

In FIG. 9, ends 199 and 199' are displaced more deeply into plunger part 100 (caused by collision with internal barrel surface 143, see FIG. 11). In FIG. 10, ends 199 and 199' are fully enclosed within plunger part 100 and, resultingly, the valve portion of the valve assembly 70 is open.

Figure 7:
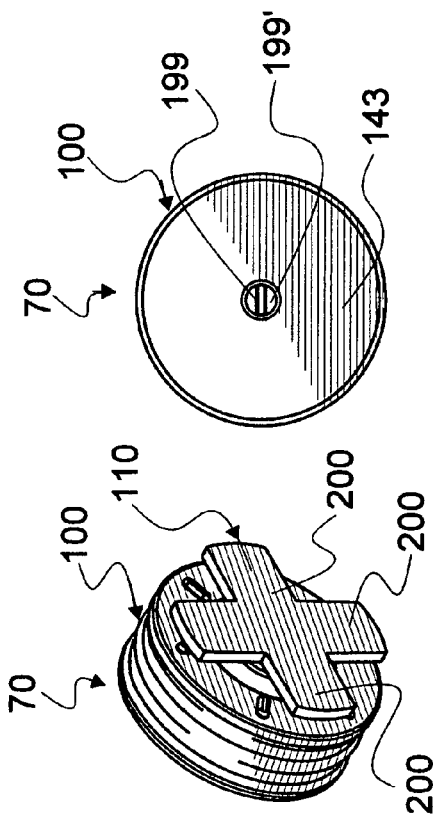
FIG. 7 is a frontal elevation of the distal face of the discharge assembly seen in FIG. 5.
Figure 6:
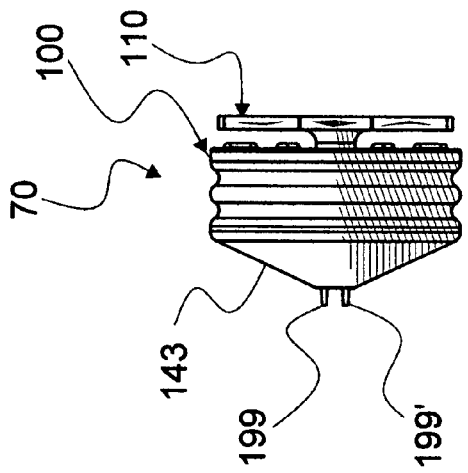
FIG. 6 is a perspective showing a proximal face of the discharge assembly seen in FIG. 5.

Reference is now made to FIG. 6 wherein a distal side of valve assembly 70 (and of plunger part 100 and valve stem 110) is seen. Note, stabilizing members, generally numbered 200 are proximally affixed to valve stem 110. Purpose and function of members 200 is disclosed in detail hereafter. As seen in FIG. 7, ends 199 and 199' are juxtaposed, but separated to demarcate duct 198.

A schematic representation of a discharge assembly 70 disposed in a syringe barrel 20 is seen in FIG. 11. Discharge assembly 70 is in a state similar to the state of discharge assembly 70 in FIG. 11 in FIGS. 5 and 8. Discharge assembly 70 is disposed proximally from internal barrel surface 143 such that an associated valve is retained in the closed state. Note that bulbous member 190 is fully contained in hole 148 and retained therein to provide a securely closed valve. Note, also, that ends 199 and 199' do not interact with any solid object while discharge assembly 70 is disposed, proximally, at a sufficient distance from surface 143 to avoid impact therewith. This permits syringe 10' to be used in the same manner as a conventional syringe until ends 199 and 199' collide and are driven proximally relative to plunger part 100.

In FIG. 12, valve assembly 70 is distally displaced, relative to the disposition of valve assembly 70 in FIG. 11, until contact is made between at least one end 199 or 199' and surface 143. Note that groove 192 remains within hole 148 of plunger portion 144, keeping the associated valve in the closed state.

Note also, that groove 192 is disposed on the distal side of bulbous member 190. So disposed, groove 192 only provides an open valve state when member 190 is more than half displaced out of hole 148 into hole 162, as may be seen in FIG. 13. Note that hole 162 must have a sufficiently large cross section such that fluid can flow around member 190.

Assurance that groove 192 is cleared when bulbous member 190 is so displaced stems from the nature of the synthetic resinous material used in plunger 100. Such material, being elastic, incompressible and resilient tends to resume a shape from which it was distorted once the cause of distortion is removed. Therefore, as bulbous member 190 is proximally displaced relative to plunger 100, resiliency of plunger 100 material tends to contract about the distal side of member 190 resulting in a proximal acceleration of bulbous member 190 and associated valve stem 110. Such acceleration acts like a forcing spring to make action of opening the valve substantially binary and permitting distal chamber to be totally cleared as plunger 100 is displaced to contact syringe barrel front surface 143. The resulting valve opening provides a fluid flow path through hole 162 and, from there, through hole 198 to be discharged from syringe barrel 20 through barrel orifice 210.

As mentioned supra, it is a principal object to retain a predetermined volume of gas disposed in a chamber proximal to the discharge assembly in the proximal chamber while dispensing only liquid from the proximal chamber. In other words, any gas resident in chamber 50 must remain in chamber 50 when liquid is dispensed therefrom. Fundamental physical properties of gas/liquid interfaces, when such a fluid mix is disposed within a cylindrical housing, provides a novel approach for delivering only liquid from a distal syringe chamber, such as chamber 50.

Reference is made to FIGS. 14-25, wherein a plot of a series of gas/liquid interfaces for various syringe barrel angular orientations relative to gravity are seen. In FIG. 14, a long axis of syringe barrel 20 is level or orthogonal to gravitational pull. Liquid, generally numbered 220, is separated from gas, generally numbered 230, across a gas/liquid interface, indicated by line 240. In FIG. 15, syringe barrel 20 is rotated counter-clockwise thirty degrees to produce a different gas/liquid interface line indication 242. Further thirty degree counter-clockwise rotation produces a gas/liquid interface line 244, seen in FIG. 16. Continued thirty degree rotation, in the same direction, yields interface line 246, as seen in FIG. 17. Another thirty degree rotation in the same direction, depicted in FIG. 18 results in interface line 248. A gas/liquid interface line 250 is seen upon another thirty degree rotation in FIG. 19.

Rotation, at thirty degree intervals, through the remaining portion of 360 degrees is seen in FIGS. 20, 21, 22, 23, 24, and 25 with respective gas/liquid interface depicting lines 252, 254, 256, 258, 260 and 262 resulting.

Figure 26:
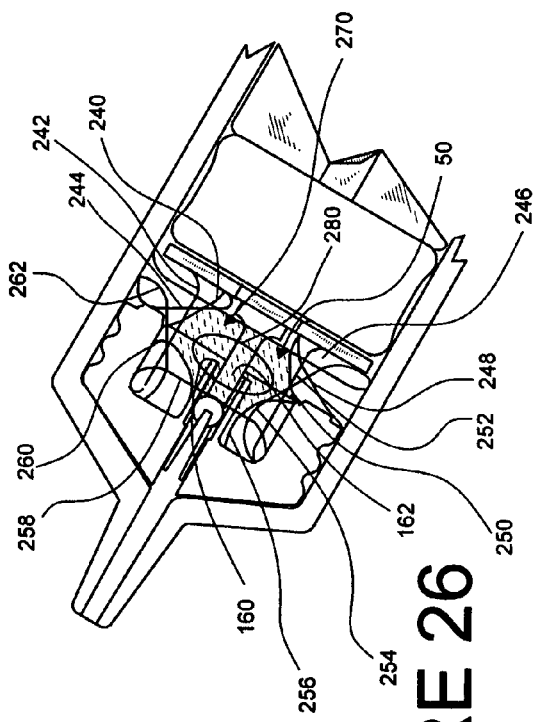
FIG. 26 is a schematic map of liquid to gas bubble interfaces seen in FIGS. 14-25 with hatching removed to permit the interfaces to be seen more clearly.

Reference is now made to FIG. 26 wherein a map is provided of the gas/liquid interface lines seen in FIGS. 14-25. It should be noted that there is a mapped gasless space 270 where no gas can exist for a predetermined gas volume. (Such a gas volume, for example, may be less than one cubic centimeter for a twenty milliliter syringe and less than one and one/half cubic centimeter for a thirty milliliter syringe.) Of course, such volumes are completely dependent upon internal syringe diameter, plunger, valve stem and plunger tip depth restrictions and other related geometries, but in all cases, there is a given, predeterminable gas volume for which a gasless space 270 exists. Such a gasless space 270 surrounds a safe liquid zone outlined by a solid volume, surrounded by an ellipsoid, which is represented by ellipse 280 in FIG. 26.

Referring again to FIG. 3, it may be noted that proximal edge 160 provides access for dispensing fluid from chamber 50 through hole 162. By disposing proximal edge 160 within the ellipsoid represented by ellipse 280, as seen in FIG. 26, only liquid 220 can be dispensed from chamber 50 and all gas 230 of the predetermined volume is retained within chamber 50 (see FIGS. 14-25). Note that retention of gas 230 generally assures no reflux at the end of a dispensing cycle. As it is critical that proximal edge 160 is continuously disposed within ellipse 280, members 200 (see FIG. 6) are affixed to support valve stem 110 and, therefore, proximal edge 160 to assure that proximal edge 160 stays in the liquid zone defined by ellipse 280.

Figure 28:
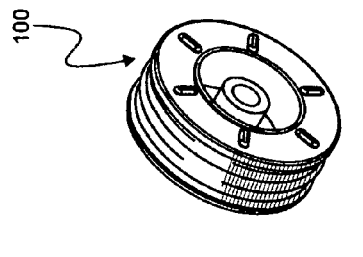
FIG. 28 is a perspective of the discharge assembly plunger seen in FIG. 27 with the hollow support cylinder inserted into a proximally disposed hollow of the plunger.
Figure 27:
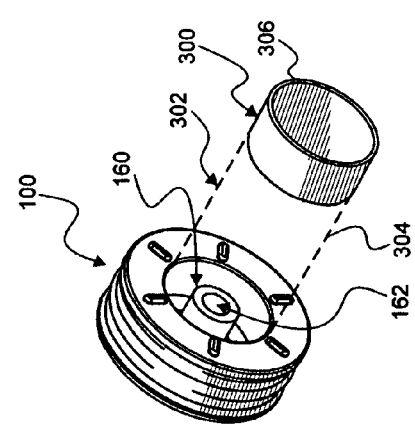
FIG. 27 is a perspective of discharge assembly plunger and a hollow support cylinder which can be inserted into the plunger.
Figure 29:
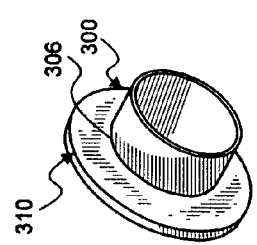
FIG. 29 is a perspective of the support cylinder seen in FIG. 28 with a support collar affixed at the proximal side.

Because plunger part 100 opens proximally, there is some jeopardy that stiction will cause leakage about ridges 136 and grooves 138 of ringed cylindrical face 134 when displacing part 100 after long term storage. To allay that possibility, a hollow support cylinder, such as cylinder 300, may be inserted into plunger 100, along dashed lines 302 and 304. An inserted cylinder 300 is seen in FIG. 28. Further, on a proximal side 306 of cylinder 300, a collar 310 may be raised (as seen in FIG. 29) to provide additional support and stability.

This invention may be embodied in other specific forms without departing from the spirit or essential characteristics thereof. The present embodiments are therefore to be considered in all respects as illustrative and not restrictive, the scope of this invention being indicated by the appended claims rather than by the foregoing description, and all changes which come within the meaning and range of equivalency of the claims are therefore intended to be embraced therein.

What is claimed and desired to be secured by Letters Patent is:

1. A multi-chamber syringe apparatus for sequentially dispensing medical fluids from a proximal and a distal chamber of the syringe, said apparatus comprising:
   a barrel of a conventional medical syringe having a hollow cylindrical wall having an internal surface which is concentrically disposed about an elongated medial axis, said barrel surface comprising an open proximal end and a distal end having a closed interior about an orifice through which fluid is transferred;
   a plunger rod and plunger tip combination disposed to be displaced within said barrel by application of a directional force against said plunger rod for dislocating fluid thereby;
   a discharge assembly comprising a stopper which, when disposed within said barrel between said plunger combination and said distal end, provides a proximal chamber between the discharge assembly and plunger tip and a disparate distal chamber between the discharge assembly and said closed interior surface;
   said proximal chamber comprising space for fluid which comprises a volume of gas which does not exceed a predetermined volume, filling only a portion of the chamber thereby, and a volume of liquid which fills space in the proximal chamber not taken by the gas;
   said discharge assembly stopper comprising a normally closed valve having a part which effects opening of the valve by being displaced proximally relative to the rest of the discharge assembly, said part being so displaced upon collision with the distal end of the syringe and as a consequence of accelerating compressive forces between the wall and the discharge assembly stopper;
   said discharge assembly stopper further comprising structure which provides access to a liquid zone which is void of the gas within the proximal chamber; and
   said discharge assembly stopper structure further comprising a hollow, proximally-extending conduit sleeve, wherethrough liquid flows from the proximal chamber through the normally closed valve, once opened, and an associated conduit sleeve access portal disposed within the liquid zone whereby only liquid flows into the conduit sleeve and, therefore, from the proximal chamber when dispensing fluid from the proximal chamber subsequent to dispensing fluid from the distal chamber and the predetermined volume of gas is retained within the proximal chamber.

2. A multi-chamber syringe apparatus for sequentially dispensing medical fluids, said apparatus comprising:
   a syringe barrel having a hollow cylindrical wall having an internal surface which is concentrically disposed about an elongated medial axis, said barrel surface comprising an open proximal end and a distal end having a closed interior about an orifice through which fluid is transferred;
   a plunger rod and plunger tip combination disposed to be displaced within said barrel by application of a directional force against said plunger rod for dislocating fluid thereby;
   a discharge assembly comprising a stopper which, when disposed within said barrel between said plunger combination and said distal end, provides a proximal chamber between the discharge assembly and plunger tip and a disparate distal chamber between the discharge assembly and said closed interior surface;
   said proximal chamber comprising space for fluid which comprises a volume of gas which does not exceed a predetermined volume, filling only a portion of the chamber thereby, and a volume of liquid which fills space in the proximal chamber not taken by the gas;
   said discharge assembly stopper comprising a normally closed valve having a part which effects opening of the valve by being displaced proximally relative to the rest of the discharge assembly, said part being so displaced upon collision with the distal end of the syringe and as a consequence of accelerating compressive forces between the wall and the discharge assembly stopper;
   said discharge assembly stopper further comprising structure which provides access to a liquid zone within the proximal chamber;
   said discharge assembly stopper structure further comprising a hollow, proximally-extending conduit sleeve, wherethrough liquid flows from the proximal chamber through the normally closed valve, once opened, and an associated conduit sleeve access portal disposed within the liquid zone whereby only liquid flows into the conduit sleeve and, therefore, from the proximal chamber when dispensing fluid from the proximal chamber subsequent to dispensing fluid from the distal chamber and the predetermined volume of gas is retained within the proximal chamber and
   an elongated valve stem and stopper comprising a body having a hollow interior comprising a closed distal face except for a through hole medially disposed therein, said stopper through hole being of reduced diameter distally and therefore being substantially closed to fluid flow when the valve stem is disposed, in a first state, within a distal portion of the through hole;
   said stopper further comprising the conduit sleeve affixed to the body about the through hole and extending proximally to form a continuous pathway from the through hole through the conduit sleeve, said conduit sleeve having a larger diameter than the more distally disposed through hole.

3. A multi-chamber syringe apparatus according to claim 2 wherein said elongated valve stem comprises:
   a medial section which is disposed within said through hole in a first elongated valve stem state;
   said through hole having an internal diameter such that the through hole is occluded when the medial section of the valve stem is in the first state to form the normally closed valve;
   said conduit sleeve having an expanded internal diameter relative to the diameter of the through hole to provide a flow pathway therethrough when the medial section is therein disposed in a second elongated valve stem state;
   said valve stem having a distal section which protrudes from the distal face to first communicate with the distal end of the syringe and thereby be displaced proximally relative to the stopper body upon collision with the distal end of the syringe to a second elongated valve stem state whereat the through hole is no longer occluded to thereby open the through hole and conduit sleeve for liquid flow from the proximal chamber.

4. A valve assembly for providing a liquid-only dispensing multi-chamber syringe within a conventional medical syringe which has a conventional plunger and stem which is displace through a barrel having a continuous, smooth internal surface which is concentrically disposed about an elongated medial axis, said barrel surface comprising an open proximal end and a distal end having a closed interior about an orifice through which fluid is transferred, said valve assembly dividing the syringe barrel into a distal chamber defined distally by the orifice and proximally by the valve assembly and a proximal chamber defined distally by the valve assembly and proximally by the plunger, the proximal chamber being filled with fluid comprising liquid, a portion of which is physically constrained to be disposed in a liquid zone, and a predetermined volume of gas which is kept by physical forces associated with liquid and gas states away from the liquid zone, said valve assembly comprising:

a normally closed valve comprising a part which effects opening of the valve by being displaced proximally relative to the rest of the valve assembly, said part being so displaced upon contact against said distal end of the barrel to provide a fluid pathway from the proximal chamber to the syringe orifice;

a conduit sleeve providing access between the pathway and the liquid zone, thereby restricting dispensing of fluid from the proximal chamber to liquid only, the gas portion of the fluid being retained within the syringe barrel and, thereby, not delivered from the proximal chamber.

* * * * *